US005549103A

United States Patent [19]
Johnson

[11] Patent Number: 5,549,103
[45] Date of Patent: *Aug. 27, 1996

[54] NASAL DILATOR HAVING AN ADHESIVE VOID TO ALLOW RELATIVE MOVEMENT

[75] Inventor: Bruce C. Johnson, St. Paul, Minn.

[73] Assignee: Creative Integration & Design, Inc., St. Paul, Minn.

[*] Notice: The term of this patent shall not extend beyond the expiration date of Pat. No. 5,533,053.

[21] Appl. No.: 316,636

[22] Filed: Sep. 30, 1994

Related U.S. Application Data

[63] Continuation of Ser. No. 50,557, Apr. 20, 1993, abandoned, and a continuation-in-part of Ser. No. 183,916, Jan. 19, 1994, which is a continuation of Ser. No. 48,589, Apr. 16, 1993, abandoned, which is a continuation of Ser. No. 884,626, May 15, 1992, abandoned, which is a continuation of Ser. No. 712,508, Jun. 10, 1991, abandoned, said Ser. No. 50,557, is a continuation-in-part of Ser. No. 48,589.

[51] Int. Cl.⁶ .............................. A61F 5/08; A61F 5/56; A61M 15/08; A62B 7/00
[52] U.S. Cl. .............. 128/200.24; 128/848; 128/204.12; 128/207.18; 606/204.45; 602/902
[58] Field of Search ...................... 128/200.24, 207.18, 128/848, 857, 858, 912, DIG. 26, 204.12; 602/5, 6, 12, 14, 16, 17, 46, 47, 60, 61, 74, 902; 606/191, 196, 199, 201, 204.15, 204.45

[56] References Cited

U.S. PATENT DOCUMENTS

| 850,978 | 4/1907 | Soares | 128/163 |
|---|---|---|---|
| 1,043,924 | 11/1912 | Gottlieb | 606/199 |
| 1,292,083 | 1/1919 | Sawyer | 606/199 |
| 1,950,839 | 3/1934 | Chirila | 606/199 |
| 2,001,862 | 5/1935 | Battey | 128/163 |
| 2,398,073 | 4/1946 | Bonde | 128/87 R |
| 2,509,157 | 5/1950 | Lind | 128/87 |
| 3,046,989 | 7/1962 | Hill | 128/207.18 |
| 3,426,751 | 2/1969 | Radewan | 128/76 C |
| 3,742,943 | 7/1973 | Malmin | 128/76 C |
| 3,835,848 | 9/1974 | Berner | 128/76 C |
| 3,935,859 | 2/1976 | Doyle | 128/89 |
| 4,153,051 | 5/1979 | Shippert | 128/89 |
| 4,213,452 | 7/1980 | Shippert | 128/89 |
| 4,274,402 | 6/1981 | Shippert | 128/89 |
| 4,340,040 | 7/1982 | Straith | 128/76 C |
| 4,402,314 | 9/1983 | Goode | 128/87 R |

(List continued on next page.)

FOREIGN PATENT DOCUMENTS

| 437661 | 11/1926 | Germany | 128/76 C |
|---|---|---|---|
| 12987 | 9/1899 | United Kingdom | 128/76 C |
| WO92/22340 | 12/1992 | WIPO . | |

OTHER PUBLICATIONS

CoNco Article "Nasal Splint", p. 12, Oct. 10, 172.

*Primary Examiner*—Kimberly L. Asher
*Attorney, Agent, or Firm*—Kinney & Lange, P.A.

[57] ABSTRACT

A nasal dilator that prevents the outer wall tissue of the nasal passages of the nose from drawing in during breathing comprises a truss member. The truss member includes a flexible strip of base material having a first end region, a second end region and an intermediate segment. The first and second end regions are adapted to engage the outer wall tissue of first and second nasal passages of the nose. The intermediate segment is configured to traverse a portion of a nose located between the first and second nasal passages. The truss member further includes first and second resilient bands secured to the strip of material adjacent opposite edges of the intermediate segment. The resiliency of the first and second resilient bands acts to stabilize the outer wall tissue and thereby prevents the outer wall tissue of the first and second nasal passages from drawing in during breathing. The truss member further includes an attachment void region located between the resilient bands and the strip of base material. The attachment void region allows for redirection of distortion forces imparted to the truss member, by allowing those portions of the first and second resilient bands above the attachment void region to rise off of the nose bridge.

13 Claims, 4 Drawing Sheets

U.S. PATENT DOCUMENTS

| | | | |
|---|---|---|---|
| 4,414,977 | 11/1983 | Rezakhany | 128/342 |
| 4,534,342 | 8/1985 | Paxa | 182/163 |
| 4,674,133 | 6/1987 | Oschner | 2/206 |
| 4,823,789 | 4/1989 | Beinsang, III | 128/207.18 |
| 4,932,943 | 6/1990 | Nowak | 604/180 |
| 4,984,302 | 1/1991 | Lincoln | 2/206 |
| 4,995,114 | 2/1991 | Price Jr. | 2/15 |
| 5,003,971 | 4/1991 | Buckley | 128/156 |
| 5,022,389 | 6/1991 | Brennan | 128/858 |
| 5,101,837 | 4/1992 | Perrin | 128/888 |

NASAL DILATOR HAVING AN ADHESIVE VOID TO ALLOW RELATIVE MOVEMENT

This is a continuation of the application having Ser. No. 08/050,557, filed on Apr. 20, 1993, now abandoned, which was the continuation-in-part of the application having Ser. No. 08/048,589, filed on Apr. 16, 1993, now abandoned, which was a continuation of the application having Ser. No. 07/884,626, filed on May 15, 1992, now abandoned which was a continuation of the application having Ser. No. 07/712,508, filed on Jun. 10, 1991, now abandoned. This is also a continuation-in-part of application Ser. No. 08/183,916, filed Jan. 19, 1994, which is a continuation of application Ser. No. 08/048,589, filed Apr. 16, 1993, now abandoned, which is a continuation of application Ser. No. 07/884,626, filed May 15, 1991, now abandoned which is a continuation of application Ser. No. 08/712,508, filed Jun. 10, 1991, now abandoned.

REFERENCE TO RELATED APPLICATIONS

Reference is made to U.S. patent application Ser. No. 07/884,626 filed on May 15, 1992 which is a Continuation of U.S. patent application Ser. No. 07/712,508 filed on Jun. 10, 1991 entitled NASAL DILATOR which is incorporated herein by reference thereto. Reference is further made to U.S. patent application Ser. No. 08/050,554 entitled NASAL DILATOR filed on even date herewith which is incorporated herein by reference thereto.

BACKGROUND OF THE INVENTION

This invention relates generally to the field of devices for the treatment of malformations. In particular, the present invention is a nasal dilator for preventing outer wall tissue of nasal passages of a nose from drawing in during breathing.

A portion of the human population has some malformation of the nasal passages which makes breathing difficult. Example of such malformations are a deviated septum and swelling due to allergic reactions. The lower portion of the nostril, immediately above the entrance to the nostril, is known as a vestibule. The vestibule tapers inwardly to a narrowed neck-like area called the nasal valve. Posterior to the nasal valve the nasal passages widen out again. Nasal obstructions commonly occur at the nasal valve in individuals who have swelling due to allergic reactions, a deviated septum or similar condition, to the point that the nasal valve may be substantially blocked. Commonly, the lateral wall (i.e., the outer wall tissue of the nasal passage) at the nasal valve is loose with the result that the outer wall tissue draws in during the process of inhalation to substantially or completely block the passage of air through the nasal passage.

Blockage of the nasal passages is obviously an inconvenience to persons who experience it. In particular, sustained mouth breathing over a long period of time may cause lung irritation due to the inhalation of foreign particles that would otherwise be filtered if the breath had been passed through the nose. Blockage of the nasal passages is particularly uncomfortable at night, since it is uncomfortable for many people who have such a problem to breathe through the mouth while asleep. Nasal blockage can lead to sleep disturbances, sleep irregularities and/or snoring. In addition, a person with such a condition may wake often because he/she is not inhaling sufficient quantities of oxygen.

The most common approach to a serious and chronic nasal blockage problem as described above is a surgical attempt to correct the malformation of the nasal passages. However, surgery is expensive and may not ultimately correct the problem.

As an alternative to surgery, nasal dilators for aiding breathing through the nose are generally known. U.S. Pat. No. 4,414,977 to Rezakhany discloses one such nasal dilator. The nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the nasal valve within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing.

However, these nasal dilators are not always effective since they are uncomfortable to wear. Because the nasal dilators must be inserted within the nasal passages they may cause irritation and itching. In addition, these nasal dilators must be custom-made to fit each nasal passage of an individual.

Another nasal dilator is disclosed in the U.S. Pat. No. 1,292,083 to Sawyer. This nasal dilator includes pads of adhesive material to which are attached metal loops. The pads are applied to the exterior surface of the nose above the nostrils. Once the pads are affixed, a dilating member is connected with each of the loops. The dilating member consists of a metal wire that provides a spring force which is directed outwardly or upwardly when hooked ends of the dilating member are engaged with the loops of the pads. A further nasal dilator is disclosed in the U.S. Pat. No. 1,950,839 to Chirila. This nasal dilator is similar to that of Sawyer but employs suction cups to secure a dilating member to the exterior surface of the nose.

These nasal dilators are not always effective in insuring free breathing because of their multiple element configurations that are designed to be assembled and then disassembled. Because these dilators are meant to be readily assembled and disassembled, the dilating members can easily become disengaged from the elements (i.e., the pads in Sawyer and the suction cups in Chirila) that secure the dilating members to the exterior of the nose. This unwanted disengagement of the elements could result in injury to the face or eyes of the wearer of the nasal dilators. Injury to the face and eyes is particularly likely during sleep, when the dilators are most likely worn since the wearer of the dilators, during any rolling over or the like, has little conscious control or awareness of the assembled or disassembled state of the dilators.

A still further nasal dilator is disclosed in the International Application Published Under The Patent Cooperation Treaty WO 92/22340 to Johnson. This nasal dilator comprises a truss member that includes a flexible strip of material having a first end region, a second end region and an intermediate segment. The first and second end regions are adapted to engage the outer wall tissue of first and second nasal passages of the nose and are secured thereto via an adhesive substance. The intermediate segment traverses the bridge of the nose. The truss member further includes resilient bands that are secured to the strip of material by way of strips of double sided adhesive foam tape. The resiliency of the bands acts to stabilize the outer wall tissue and thereby prevents the outer wall tissue of the nasal passages from drawing in during breathing.

In the International Application, a padded element is secured to the median of the intermediate segment of the strip of material via the adhesive substance. The padded element creates an absorbative adhesive void between the truss member and the bridge of the nose. The absorbative adhesive void absorbs moisture due to perspiration, or the like. The adhesive void also allows for redirection of resulting forces in the truss member caused by forces (which push the skin of the nose up along the outer wall cartilage of the nose) occurring when one side of the nose or face of the wearer is distorted from its normal or relaxed position, by such actions as wiping the nose or face, facial gestures or sleeping with part of the nose or face against a pillow. The absorbative adhesive void allows for transference (i.e., redirection) of these resulting distortion forces in the truss member, which are imparted to the truss member via contact with an object, facial gestures, etc., by allowing that portion of the nasal dilator with the adhesive void to rise off of the bridge of the nose.

By allowing the nasal dilator to rise off the nose bridge, the adhesive void substantially reduces the transference of truss member motion, from the end of the truss member upon which distortion forces are acting, along the truss member over the bridge of the nose, and to the opposite end of the truss member (and thereby to the skin on the opposite side of the nose), that would occur absent the adhesive void (i.e., if the truss member were adhesively secured to the bridge of the nose). This transference of distortion forces from one end of the truss member, along the truss member and to the other end of the truss member may cause wearer skin distortion due to increased shear and peel forces at the adhesive interface to the skin. This skin distortion may be uncomfortable to some wearer's. Further, by allowing the nasal dilator to rise off the nose bridge, the adhesive void eliminates upward pulling forces on the skin of the bridge of the nose, that might otherwise occur if the intermediate segment of the strip of material were adhesively secured to the nose bridge. However, the raising and lowering of the adhesive void (i.e., padded element) at the bridge of the nose stimulates the skin on the nose bridge, which some wearer's of the nasal dilator perceive as an irritating itch. This itching sensation felt by some wearer's may cause some wearer's to perceive the dilator as uncomfortable.

It is evident that there is a continuing need for improved nasal dilators for preventing outer wall tissue of nasal passages of a nose from drawing in during breathing. Specifically, there is a need for a nasal dilator that can provide effective relief without the need of inserting an object within the nasal passage. Moreover, there is a need for a nasal dilator that can be reliably worn at night when the nasal blockage problem is most acute and most uncomfortable. In addition, there is a need for a nasal dilator that can be reliably worn through extended therapeutic periods. The nasal dilator should be of efficient design and relatively uncomplicated. In addition, the nasal dilator should provide effective stabilization of the outer wall tissue of the nasal passages to provide effective relief from nasal blockage during inhalation. Moreover, this effective stabilization should be provided without undue discomfort to the wearer.

SUMMARY OF THE INVENTION

The present invention is a nasal dilator for preventing outer wall tissue of nasal passages of a nose from drawing in during breathing. The nasal dilator comprises a truss member having a first end region, a second end region and an intermediate segment coupling the first end region to the second end region. An engagement means is adhered to the first and second end regions and the intermediate segment. The engagement means secures the first end region to the outer wall tissue of a first nasal passage, the second end region to the outer wall tissue of a second nasal passage and the intermediate segment to a portion of a nose located between the first and second nasal passages. A resilient means extends along the first end region, the second end region and the intermediate segment and acts to stabilize the outer wall tissue and thereby prevent the outer wall tissue of the first and second nasal passages from drawing in during breathing. A further means permits the resilient means, at least in part, to move relative to another portion of the truss member, to redirect forces imparted to the truss member.

The truss member includes a flexible strip of material that defines the first and second end regions and the intermediate segment of the nasal dilator. A first resilient band of the resilient means is secured to a first side of the strip of material adjacent a first edge of the material. A second resilient band of the resilient means is spaced from the first resilient band is secured to the first side of the strip of material adjacent a second edge thereof. The first and second resilient bands are secured only to the first and second end regions of the flexible strip of base material, creating a void region between the resilient bands and the intermediate segment of the strip of base material. The void region redirects deflection forces imparted to the truss member via contact with an object, by allowing those portions of the first and second resilient bands above the void region to rise off of that portion of a nose located between the first and second nasal passages.

The first and second resilient bands are oriented generally parallel to one another and substantially parallel to the longitudinal extent of the strip of base material. The resiliency of the first and second resilient bands prevents the outer wall tissue of the first and second nasal passages from drawing in during breathing.

The truss member further includes an adhesive substance located on a second side of the flexible strip of material. The adhesive substance acts to releasably secure the truss member to the outer wall tissue of the first and second nasal passages. First and second release liners cover the adhesive substance on the second side of the flexible strip of base material. The first and second release liners are readily removable from the strip of base material to expose the adhesive substance and permit the truss member to be secured to the outer wall tissue of the first and second nasal passages.

This nasal dilator is an efficient, comfortable design that effectively prevents the outer wall tissue of the first and second nasal passages of the nose from drawing in during breathing. In addition, the nasal dilator provides effective relief of nasal blockage during inhalation without the irritation and discomfort normally associated with nasal dilators that are inserted within the nasal passages. By effectively relieving nasal blockage, the nasal dilator can reduce snoring sometimes associated with nasal blockage conditions. Moreover, this nasal dilator can be reliably worn at night when the inhalation nasal blockage problem is most acute, without the anxiety and inconvenience normally associated with custom made, internally worn nasal dilators or multi-element nasal dilators. In addition, the nasal dilator can be comfortably worn through extended therapeutic periods.

DETAILED DESCRIPTION OF THE PREFERRED EMBODIMENTS

Figure 1:
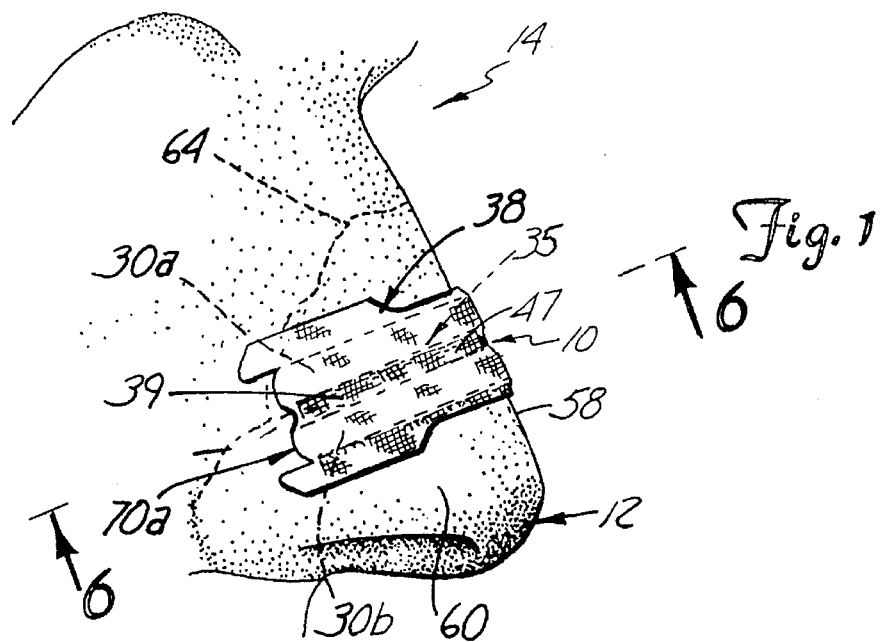
FIG. 1 is perspective view of a portion of a face with a nasal dilator in accordance with the present invention secured to a nose.

A nasal dilator 10 in accordance with the present invention is illustrated generally in FIG. 1. The nasal dilator 10 is shown secured to a nose 12 of a wearer 14.

Figure 2:
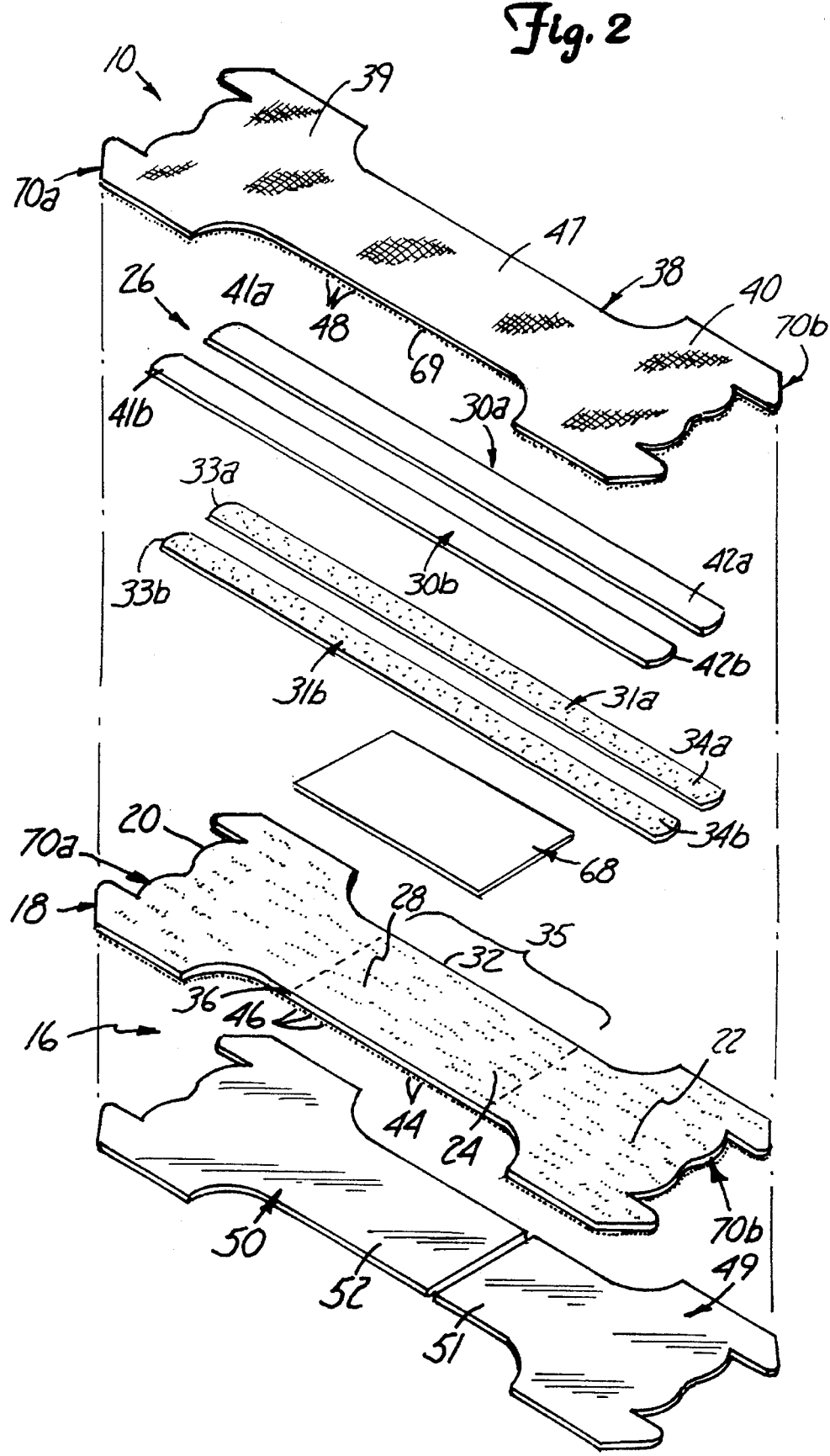
FIG. 2 is an exploded perspective view showing the components of the nasal dilator in accordance with the present invention.

As seen in FIG. 2, the nasal dilator 10 comprises a unitary truss member 16 including a flexible strip of base material 18 having a first end region 20 and a second end region 22 coupled to the first end region 20 by way of an intermediate segment 24. The width of the intermediate segment 24 is less than the width of the first and second end regions 20 and 22. The flexible strip of base material 18 is preferably formed of a polyester fabric that allows the skin of the nose 12 to breathe to maximize comfort and minimize irritation. A suitable nonwoven, spunlaced, 100% polyester, fabric from which to form the base material 18 is available from E. I. DuPont Nemours & Co. (Old Hickory, Tenn.) under the tradename SONTARA®. SONTARA®, typically has a breaking strength property on a ratio of approximately 2:1 as determined by the machine direction (MD) (i.e., warp) relative to the cross direction (XD) (i.e., filling) of the fabric. In addition, SONTARA®, typically has an elongation percentage ratio of approximately 3:1 as determined by XD/MD of the fabric. The MD of the fabric is parallel to the longitudinal extent of the strip of base material 18.

The unitary truss member 16 further includes resilient means 26 secured to a first side 28 of the strip of base material 18. The resilient means 26 includes a first resilient band 30a and a second resilient band 30b. The first resilient band 30a has a first end 41a and a second end 42a. The second resilient band 30b has a first end 41b and a second end 42b. The first and second resilient bands 30a and 30b are each formed of a plastic material. For example, an industrial grade, biaxially oriented polyester that is approximately 0.080" to 0.135" wide and 0.010" thick. The relatively slight thickness of the material of each of the first and second resilient bands 30a and 30b enhances the axial, torsional flexibility of each of the first and second resilient bands 30a and 30b about the longitudinal extent of each of the bands 30a and 30b.

The first and second resilient bands 30a and 30b are secured by first and second, flexible strips of interface adhesive material 31a and 31b, to the first side 28 of the strip of base material 18 only at the first and second end regions 20 and 22. The first strip of interface adhesive material 31a has a first end 33a and a second end 34a. The second strip of interface adhesive material 31b has a first end 33b and a second end 34b. The first and second strips of interface adhesive material 31a and 31b are of the same size and shape as the first and second resilient bands 30a and 30b, respectively.

As seen best in FIG. 2, the truss member 16 further includes a strip of flexible, porous tissue material 68 that is substantially of the same size and shape as the intermediate segment 24 of the strip of base material 18. The first resilient band 30a is secured, via the strip of adhesive material 31a, only to the end regions 20 and 22 of strip of base material 18 adjacent a first edge 32 of the intermediate segment 24. The second resilient band 30b is spaced from the first resilient band 30a, and is secured, via the strip of adhesive material 31b, only to the end regions 20 and 22 of the strip of base material 18 adjacent a second edge 36 of the intermediate segment 24. Because the tissue material 68 is interposed between the strips of interface adhesive material 31a, 31b and the intermediate segment 24 of the strip of base material 18, the resilient bands 30a, 30b are not secured to that portion of the intermediate segment 24 of the strip of base material 18 corresponding to the tissue material 68. Therefore, that portion of the intermediate segment 24 corresponding to the tissue material 68, defines an adhesive void region 35 between the first and second strips of interface adhesive material 31a and 31b, and therewith resilient bands 30a and 30b, and the intermediate segment 24 of the strip of base material 18. The first and second resilient bands 30a and 30b are oriented generally parallel to one another and substantially parallel to the longitudinal extent of the flexible strip of base material 18. Each of the flexible strips of interface adhesive material 31a and 31b is preferably an acrylic, pressure sensitive bio-compatible adhesive material, such as (3M 1509) available from Minnesota, Mining & Manufacturing, Inc. (St. Paul, Minn.).

The unitary truss member 16 further includes a flexible strip of top material 38 having a first end region 39, a second end region 40 and an intermediate segment 47, that are of the same size and shape as the first end region 20, second end region 22 and intermediate segment 24, respectively, of the strip of base material 18. A bottom surface 69 of the strip of top material 38 includes a layer of an adhesive substance 48 that extends over the first and second end regions 39 and 40 and the intermediate segment 47. The adhesive substance 48 is a breathable, acrylic, pressure sensitive, bio-compatible adhesive. The strip of top material 38 covers and is secured to the first and second resilient bands 30a and 30b and the tissue material 68 via the adhesive substance 48. The strip of top material 38 is also secured to the first side 28 of the strip of base material 18, via the adhesive substance 48, only at end regions 20 and 22. The strip of top material 38 is not secured to the intermediate segment 24 of the strip of base material 18 at the void region 35 which corresponds to the tissue material 68. The strip of top material 38 helps to prevent the first and second resilient bands 30a and 30b from readily separating from the end regions 20 and 22 of the strip of base material 18 and the strips of interface adhesive material 31a and 31b when the unitary truss member 16 is flexed. The flexible strip of top material 38 is preferably a breathable, nonwoven material, such as (3M 1533) available from Minnesota, Mining & Manufacturing, Inc. (St. Paul, Minn.).

As seen in FIG. 2, a second side 44 of the strip of base material 18 includes a layer of an adhesive substance 46 that extends over the first and second end regions 20 and 22 and the intermediate segment 24. The adhesive substance 46 is a breathable, acrylic, pressure sensitive bio-compatible adhesive. Readily removable, first and second release liners 49 and 50, respectively, cover the adhesive substance 46 on the first and second end regions 20 and 22, respectively, of the strip of base material 18. Extensions 51 and 52 of the first and second release liners 49 and 50, respectively, cover the adhesive substance 46 on the intermediate segment 24 of the strip of base material 18. The first and second release liners 49 and 50 cover the adhesive substance 46 and remain in place on the strip of base material 18 until the nasal dilator 10 is to be used.

Figure 3:
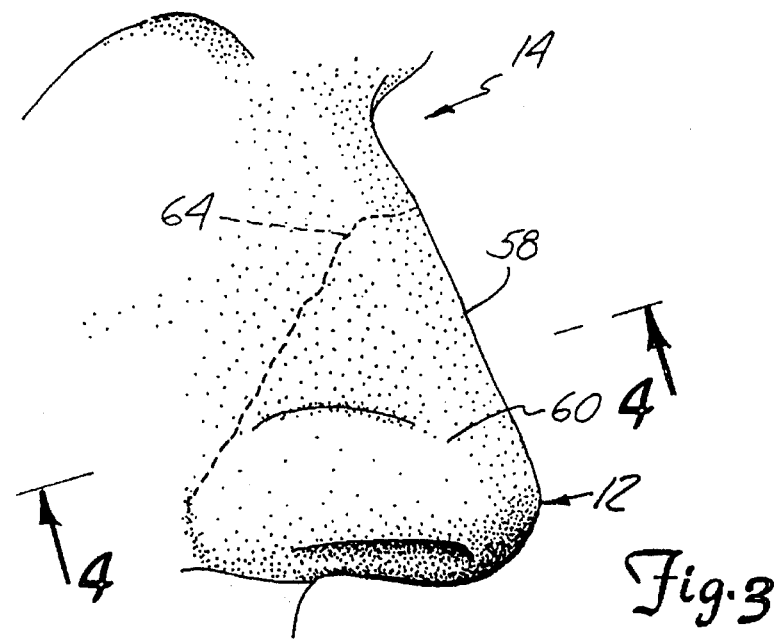
FIG. 3 is a perspective view similar to FIG. 1 with the nasal dilator in accordance with the present invention removed from the nose.
Figure 4:
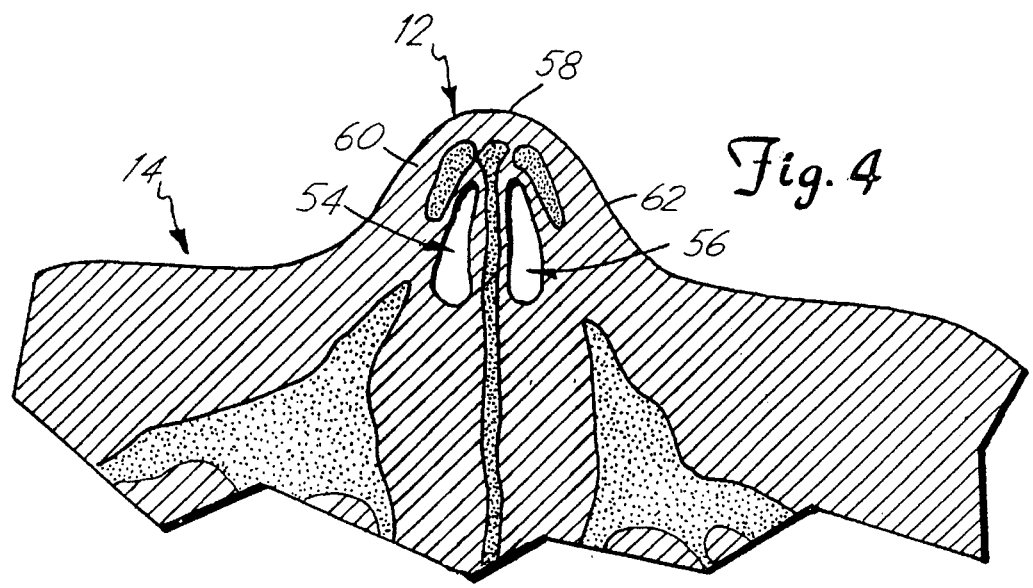
FIG. 4 is a sectional view taken along line 4—4 in FIG. 3 showing the nose in a state wherein no appreciable flow of air is occurring in the nasal passages.
Figure 5:
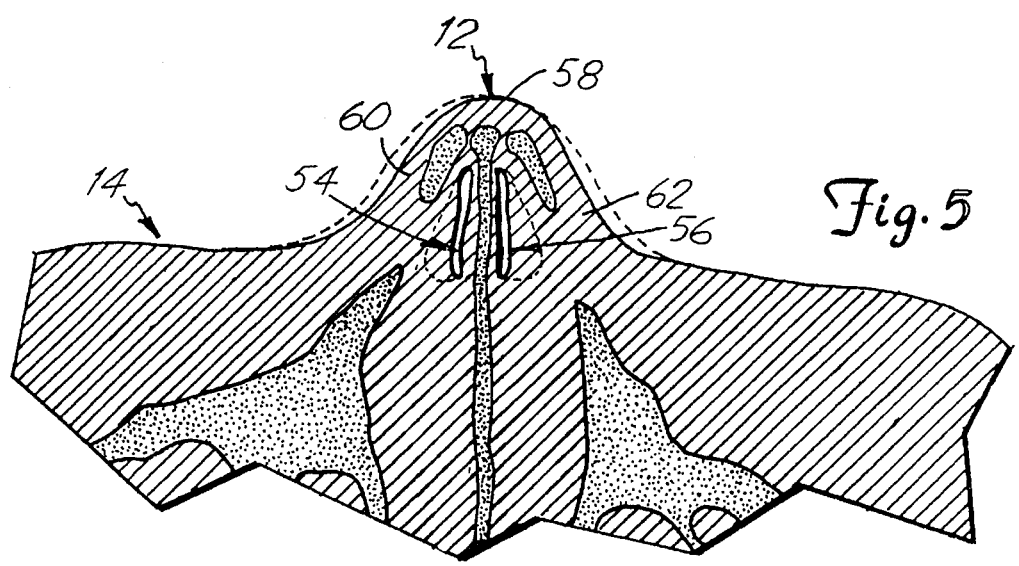
FIG. 5 is a sectional view similar to FIG. 4 showing the state of the nose during inhalation.

As seen in FIGS. 3 and 4, the nose 12 includes a first nasal passage 54, a second nasal passages 56 and a portion of the nose 12 known as the bridge 58 located between the first and second nasal passages 54 and 56. FIG. 4 shows the state of the first and second nasal passages 54 and 56 when no appreciable flow of air is occurring through the nasal passages 54 and 56. Due to a malformation, such as a deviated septum or swelling due to allergic reactions, outer wall tissue 60 and 62 of the first and second nasal passages 54 and 56, respectively, tends to be drawn in (i.e., collapse) during inhalation (see FIG. 5). This drawing in during inhalation is caused by reduced air pressure within the first and second nasal passages 54 and 56 as a result of an increase in air velocity as the in drawn breath travels through the narrowing of the nasal valves within the first and second nasal passages 54 and 56. The portion of the outer wall tissue 60 and 62 drawn in during inhalation is that located between the nasal bone 64 (shown in dashed lines in FIGS. 1 and 3) and the entrance to the nasal passages 54 and 56. This drawing in of the outer wall tissue 60 and 62 causes nasal blockage. The severity of the nasal blockage condition depends upon how narrow the nasal valve is at the outset. The nasal dilator 10 of the present invention remedies this nasal blockage problem.

Figure 6:
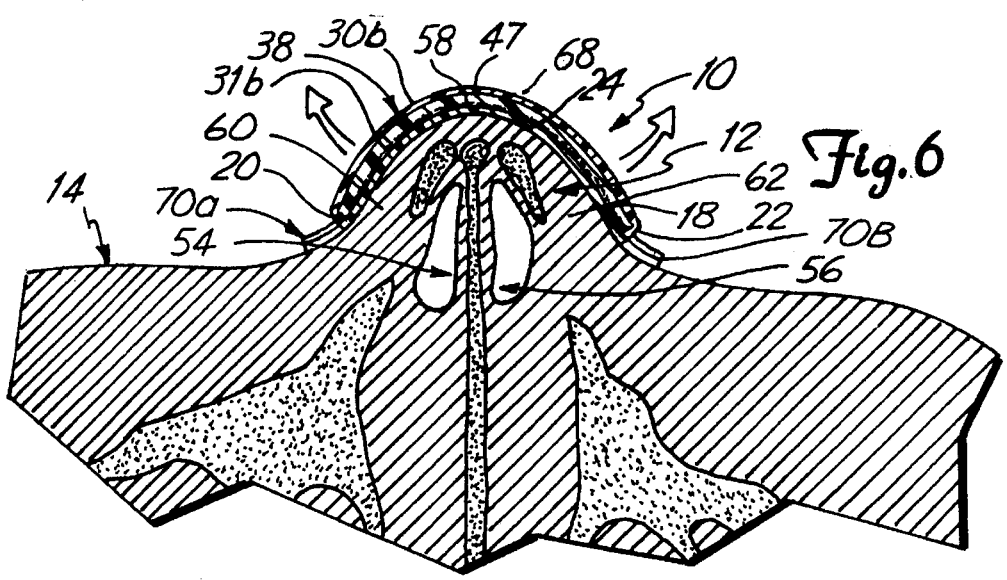
FIG. 6 is a sectional view taken along line 6—6 in FIG. 1 showing the state of the nose during inhalation with the nasal dilator in accordance with the present invention secured thereto.

To secure the nasal dilator 10 to the nose 12, the first and second release liners 49 and 50 are removed from the flexible strip of base material 18 to expose the adhesive substance 46. As seen in FIGS. 1 and 6, the nasal dilator 10 is placed on the exterior of the nose 12 such that the intermediate segment 24 traverses the bridge 58 of the nose 12 and the first and second end regions 20 and 22 contact the outer wall tissue 60 and 62 of the first and second nasal passages 54 and 56. The adhesive substance 46 on the first and second end regions 20 and 22 and the intermediate segment 24 releasably secures the unitary truss member 16 to the outer wall tissue 60 and 62 of the first and second nasal passages 54 and 56 and to the bridge 58 of the nose 12.

With the nasal dilator 10 in place about the nose 12, the resiliency of the first and second resilient bands 30a and 30b (i.e., the tendency of the resilient bands to return to their normally planar state shown in FIG. 2) acts to stabilize the outer wall tissue 60 and 62 and thereby prevents the outer wall tissue 60 and 62 of the first and second nasal passages 54 and 56 from drawing in during breathing (i.e., during inhalation). Moreover, the flexibility of the base material 18, strips of interface adhesive material 31a and 31b and top material 38, the resiliency of the first and second bands 30a and 30b, and the flexibility of the first and second resilient bands 30a and 30b due to the relatively slight thickness of the material of the bands 30a and 30b, all allow the nasal dilator 10 to closely conform to the curves of the nose of each individual wearer. The relatively slight thickness of the material of the bands 30a and 30b also enhances axial, torsional flexibility of the truss member 16 about the longitudinal extent of the truss member 16, which increases wearer comfort and facilitates adhesion of the adhesive substance 46.

In addition, the spunlaced fabric structure of the strip of base material 18, permits limited, primarily plastic and somewhat elastic deformation within the thickness of the base material 18. This limited, primarily plastic and somewhat elastic deformation property spreads out delaminating forces such as may be caused by: (1) the inherent tendency of the resilient bands to return to their normally planar state; (2) surface configuration differences between the resilient bands 30a,30 and the nose 12 of the wearer 14; and (3) displacement of the unitary truss member 16 relative to the outer wall tissue 60 and 62 as a result shear, tensile, cleavage and/or peel forces imparted at or to the outer wall tissue 60 and 62 and/or truss member 16 via wearer movement (e.g., nose gestures) and/or contact with an object (e.g., pillow); that may tend to cause the nasal dilator 10 to be inadvertently detached from the nose 12 of the wearer 14. By spreading out these delaminating forces, the strip of base material 18 acts as a buffering agent to prevent the transfer of focused forces to the adhesive substance 46 and thereby to the skin of the nose 12. Preventing the transfer of focused delaminating forces substantially eliminates any itching sensation (caused by the separation of the adhesive substance 46 from the skin) that a wearer 14 may have experienced if these delaminating forces were otherwise imparted to the skin of the nose 12.

A desired functional range of dilating force (i.e., the spring biasing force due to the resiliency of the resilient means of the nasal dilator) is typically in the range of 5 to 50 grams. Under 10 grams of dilating force is insufficient to help most wearers with any significant degree of nasal blockage upon inhalation. However, if the nasal blockage is mild enough, a positive effect may be noticed by the wearer with a little as 5 grams of dilating force provided by the dilator. A dilating force in excess of 40 grams may be somewhat obtrusive and uncomfortable for some dilator wearers.

The nasal dilator 10, of the present invention, is constructed to produce from 20 to 30 grams of dilating spring biasing force for each nasal outer wall 60 and 62. Each resilient band 30a and 30b is a portion of this total. Since two resilient bands 30a and 30b are used in the unitary truss member 16, and the resilient bands 30a and 30b are of equal proportions, each band 30a and 30b provides one half of the total designed spring biasing force.

As seen best in FIG. 1, the unitary truss member 16, defined by the base material 18, strips of interface adhesive material 31a and 31b, top material 38 and resilient bands 30 and 30b, includes a first scalloped end edge 70a and a second scalloped end edge 70b. This nasal dilator tip structure, as defined by the end edges 70a and 70b, effectively minimizes any inadvertent peeling of the end regions 20 and 22 of the strip of base material 18 from the outer wall tissue 60 and 62 of the nasal passages 54 and 56 caused by the dilating, spring biasing force exerted by the resilient bands 30a and 30b.

Figure 7:
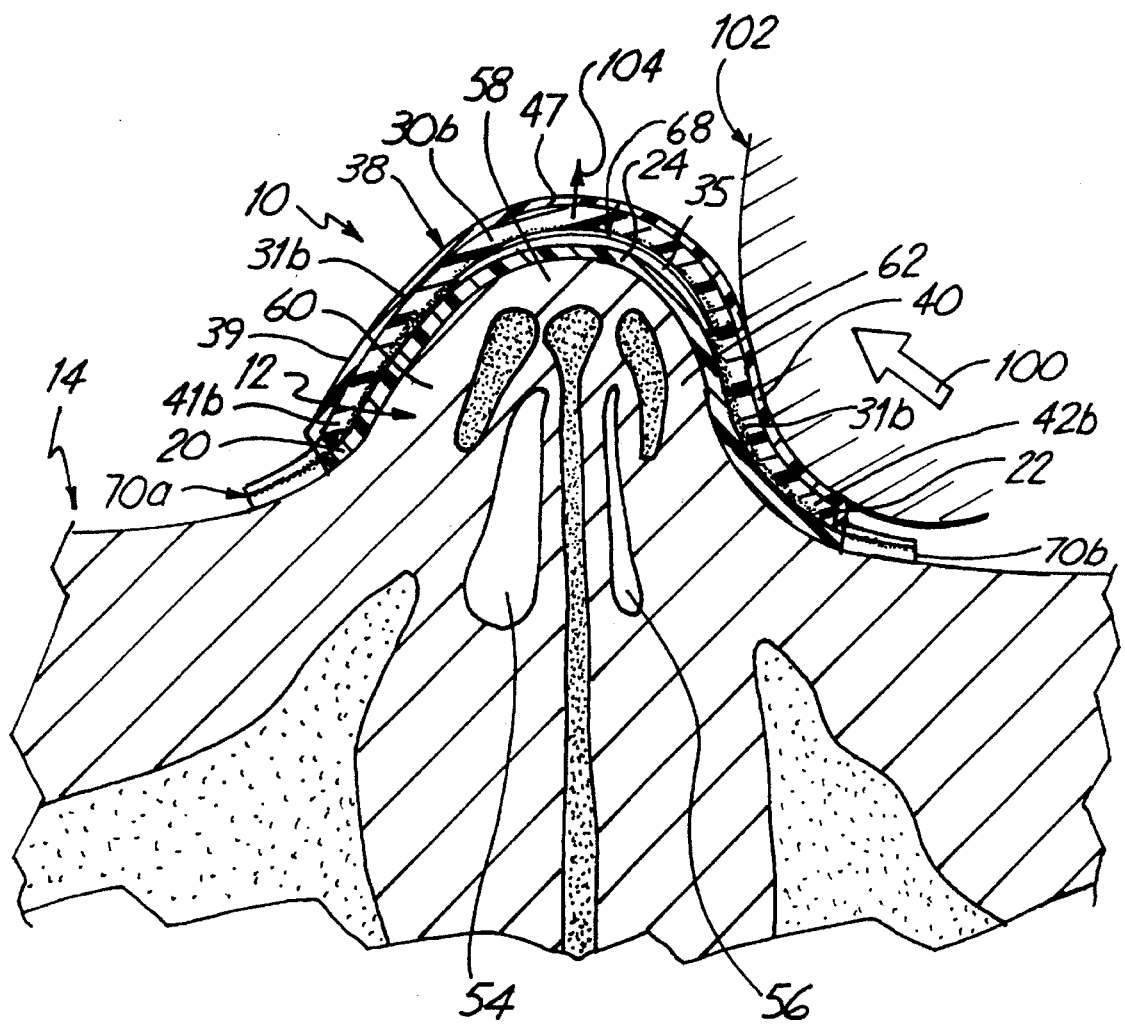
FIG. 7 is a sectional view similar to FIG. 6 illustrating how the void region of the nasal dilator of the present invention allows movement of the resilient bands relative to the strip of base material upon a force being effected upon the nasal dilator and nose.

As seen best in FIG. 7, the void region 35 allows for redirection of resulting forces in the truss member 16 caused by forces (e.g., shear, tensile, cleavage and/or peel forces which push the skin of the nose 12 up along the outer wall cartilage of the nose 12 and are represented by directional arrow 100), occurring when one side of the nose 12 or face of the wearer 14 is distorted from its normal or relaxed position (see FIG. 6), by such actions as wiping the nose 12 or face, facial gestures or sleeping with part of the nose 12 or face against an object 102, such as a pillow. The void region 35 between the resilient bands 30a,30b and the intermediate segment 24 of the strip of base material 18 allows for transference (i.e., redirection) of these resulting distortion forces (e.g., shear, tensile, cleavage and/or peel forces) in the truss member 16, which are imparted to the truss member 16 via contact with an object 102, by allowing those portions of the bands 30a,30b, that portion of the strip of top material 38 and the tissue material 68 above the void region 35 to rise (as represented by directional arrow 104) off of the bridge 58 of the nose 12.

By allowing these portions to rise off the bridge 58 of the nose 12, the void region 35 substantially reduces the transference of truss member motion, from the end region of the truss member upon which distortion forces are acting, along the truss member 16 over the bridge 58 of the nose 12, and to the opposite end region of the truss member 16 (and thereby to the skin on the opposite side of the nose 12), that would occur absent the void region 35 (i.e., if the truss member 16 were adhesively secured to the bridge 58 of the nose 12). This transference of distortion forces from one end region of the truss member 16, along the truss member 16 and to the other end region of the truss member 16 may cause wearer skin distortion due to increased shear and peel forces at the adhesive interface to the skin. This skin distortion may be uncomfortable to some wearer's. Further, by allowing these portions of the nasal dilator 10 above the void region 35 to rise off the nose bridge 58, upward pulling forces on the skin of the bridge 58 of the nose 12 are greatly reduced. However, since the strip of base material 18 is secured to the nose bridge 58, below the void region 35, at intermediate segment 24 by the adhesive substance 46, the itching sensation felt by some wearer's of prior nasal dilator designs (wherein an adhesive void was located between the nose bridge and the strip of material) is eliminated. The itching sensation is eliminated because those portions of the truss member 16 that are raised and lowered above the nose bridge 58 by deflection forces are not in direct contact with the skin of the bridge 58 of the nose 12. With the elimination of itching sensation felt by some wearer's the overall comfort of the nasal dilator 10 is substantially improved. When desired, the nasal dilator 10 can be readily, manually removed by peeling the truss member 16 from the skin of the nose 12, such as by starting at the first end region 20 and progressing over the bridge 58 of the nose 12, until the second end region 22 is also free of the nose 12.

This nasal dilator 10 is an efficient, comfortable design that effectively prevents the outer wall tissue 60 and 62 of the first and second nasal passages 54 and 56 of the nose 12 from drawing in during breathing. In addition, the nasal dilator 10 provides effective relief of nasal blockage during inhalation without the irritation and discomfort normally associated with nasal dilators that are inserted within the nasal passages. By effectively relieving nasal blockage, the nasal dilator 10 can reduce snoring sometimes associated with nasal blockage conditions. Moreover, this nasal dilator 10 can be reliably worn at night when the inhalation nasal blockage problem is most acute, without the anxiety and inconvenience normally associated with custom made, internally worn nasal dilators or multi-element nasal dilators. In addition, the nasal dilator 10 can be comfortably worn through extended therapeutic periods.

Although the present invention has been described with reference to preferred embodiments, workers skilled in the art will recognize that changes may be made in form and detail without departing from the spirit and scope of the invention.

What is claimed is:

1. A nasal dilator for preventing outer wall tissue of nasal passages of a nose from drawing in during breathing, comprising:

a truss member including:
   a first end region, a second end region and an intermediate segment coupling the first end region to the second end region;
   engagement means adhered to the first and second end regions and the intermediate segment, the engagement means securing the first end region to the outer wall tissue of a first nasal passage, the second end region to the outer wall tissue of a second nasal passage and the intermediate segment to a portion of a nose located between the first and second nasal passages;
   resilient means extending along the first end region, second end region and the intermediate segment, the resilient means acting to stabilize the outer wall tissue and thereby prevent the outer wall tissue of the first and second nasal passages from drawing in during breathing; and
   means for permitting the resilient means, at least in part, to separate from at least part of the intermediate region to redirect forces imparted to the truss member.

2. The nasal dilator of claim 1 wherein the truss member includes:
   a flexible strip of base material defining the first and second end regions and the intermediate segment.

3. The nasal dilator of claim 2 wherein the engagement means is an adhesive substance located on a second side of the flexible strip of base material at the first and second end regions and the intermediate segment thereof for releasably securing the flexible strip of base material to the outer wall tissue of the first and second nasal passages and that portion of a nose located between the first and second nasal passages.

4. The nasal dilator of claim 3, and further including:
   first and second release liners covering the adhesive substance on the first and second end regions and the intermediate segment of the flexible strip of base material, the first and second release liners being readily removable from the flexible strip of base material to expose the adhesive substance and permit the truss member to be secured to the outer wall tissue of the first and second nasal passages and that portion of a nose located between the first and second nasal passages.

5. The nasal dilator of claim 2 wherein the resilient means is secured to a first side of the flexible strip of base material at the first end region and the second end region of the strip of base material, and wherein the separation permitting means includes a lack of any attachment between the intermediate segment of the strip of base material and that portion of the resilient means immediately adjacent thereto.

6. The nasal dilator of claim 5 wherein the resilient means includes:
   a first resilient band secured to the first and second end regions of the flexible strip of base material adjacent a first edge thereof; and
   a second resilient band secured to the first and second end regions of the flexible strip of base material at a second edge thereof, the second resilient band being spaced from and extending generally parallel to the first resilient band.

7. The nasal dilator of claim 6 wherein the first and second resilient bands are secured to the first side of the flexible strip of base material by way of an interface adhesive means.

8. The nasal dilator of claim 7 wherein the interface adhesive means includes a first strip of interface adhesive material corresponding to the first resilient band and a second strip of interface adhesive material corresponding to the second resilient band.

9. The nasal dilator of claim 7 and further including:

a strip of top material that covers the first and second resilient bands and is adhesively secured only to the first and second end regions of the flexible strip of base material.

10. The nasal dilator of claim 2 wherein the resilient means includes:

at least one resilient band oriented substantially parallel to a longitudinal extent of the flexible strip of base material, the resiliency of the at least one resilient band acting to prevent the outer wall tissue of the first and second nasal passages from drawing in during breathing.

11. A nasal dilator capable of introducing separating stresses in outer wall tissues of a human nose, comprising:

a truss having a pair of spaced apart end surfaces joined by an intermediate segment such that if said spaced apart end surfaces are forced toward one another from initial positions to substantially reduce said spacing therebetween by a spacing reduction force external to said truss, restoring forces result in said truss sufficient to restore a substantial fraction of said spacing between said end surfaces absent such spacing reduction forces, said intermediate segment being at least partially divided into two connected but separable portions such that they can move with respect to one another; and an engagement means adhered to said end surfaces and capable of engaging exposed surfaces of such outer wall tissues sufficiently to remain so engaged against said restoring forces, a selected one of said intermediate segment portions joining said end surfaces.

12. The nasal dilator of claim 11 wherein the truss includes:

a flexible strip of base material defining said pair of spaced apart end surfaces and one of said intermediate segment portions; and a resilient means, at least in part, adhesively secured to a first side of said flexible strip of base material, said resilient means providing said restoring forces.

13. The nasal dilator of claim 12 wherein said intermediate segment portions are rendered separable by an adhesive void region between a portion of said resilient means, located at least in part in one of said intermediate segment portions, and said flexible strip of base material, located at least in part in that other intermediate segment portion, said adhesive void region permitting said resilient means, at least in part, to move relative to said flexible strip of base material.

* * * * *